United States Patent [19]
Alexander

[11] Patent Number: 5,254,129
[45] Date of Patent: Oct. 19, 1993

[54] ARTHROSCOPIC RESECTOR

[76] Inventor: Chris B. Alexander, 1458 26th Ave., San Francisco, Calif. 94122

[21] Appl. No.: 796,578

[22] Filed: Nov. 22, 1991

[51] Int. Cl.⁵ .......................................... A61B 17/32
[52] U.S. Cl. ................... 606/170; 606/174; 604/22; 30/135
[58] Field of Search ........... 606/167, 170, 174, 171, 606/172, 175, 166; 128/751, 752, 753, 754; 604/22; 30/245, 246, 249, 250, 257, 131, 134, 135

[56] References Cited

U.S. PATENT DOCUMENTS

| | | | |
|---|---|---|---|
| 614,167 | 11/1898 | Gardella | 30/135 |
| 887,494 | 5/1908 | Mulertz | 30/135 |
| 1,650,948 | 11/1927 | Long | 30/135 |
| 2,323,183 | 6/1943 | Alleyne | 606/174 |
| 3,006,344 | 10/1961 | Vogelfanger | 606/174 |
| 3,166,071 | 1/1965 | Mayer | 606/174 |
| 3,336,667 | 8/1967 | Wallace et al. | 30/135 |
| 4,428,374 | 1/1984 | Auburn | 606/174 |
| 4,644,651 | 2/1987 | Jacobsen | 606/174 |
| 4,648,401 | 3/1987 | Mattson | 606/174 |
| 4,674,501 | 6/1987 | Greenberg | 606/174 |

FOREIGN PATENT DOCUMENTS 0050053 9/1911 Austria .................. 606/174

*Primary Examiner*—Edgar S. Burr
*Assistant Examiner*—Christopher A. Bennett
*Attorney, Agent, or Firm*—Douglas E. White

[57] ABSTRACT

A hand-held instrument is disclosed for use in surgery. The instrument has a set of opposed jaws that pivot about a common axis with respect to a shaft of the instrument's handle. The upper jaw has an upper blade rigidly affixed to one side thereof. A lower blade is rigidly affixed to the shaft. When the upper jaw and upper blade are jointly forced to pivot downward by a push rod on the shaft, the rotating upper blade moves past the stationary lower blade to amputate a piece of tissue in scissor-cutting fashion. The lower jaw is simultaneously forced (by the interposed tissue) to rotate about its pivot downwardly, i.e. in the same direction as and in fixed tandem with the upper jaw. The lower jaw is held tightly against the interposed tissue via a stiff spring against which the lower jaw is biased. The spring causes the jaws to tightly clasp the tissue in plier-clamping fashion during and after its amputation from its attachment. The instrument is operated by a scissor handle arrangement.

12 Claims, 4 Drawing Sheets

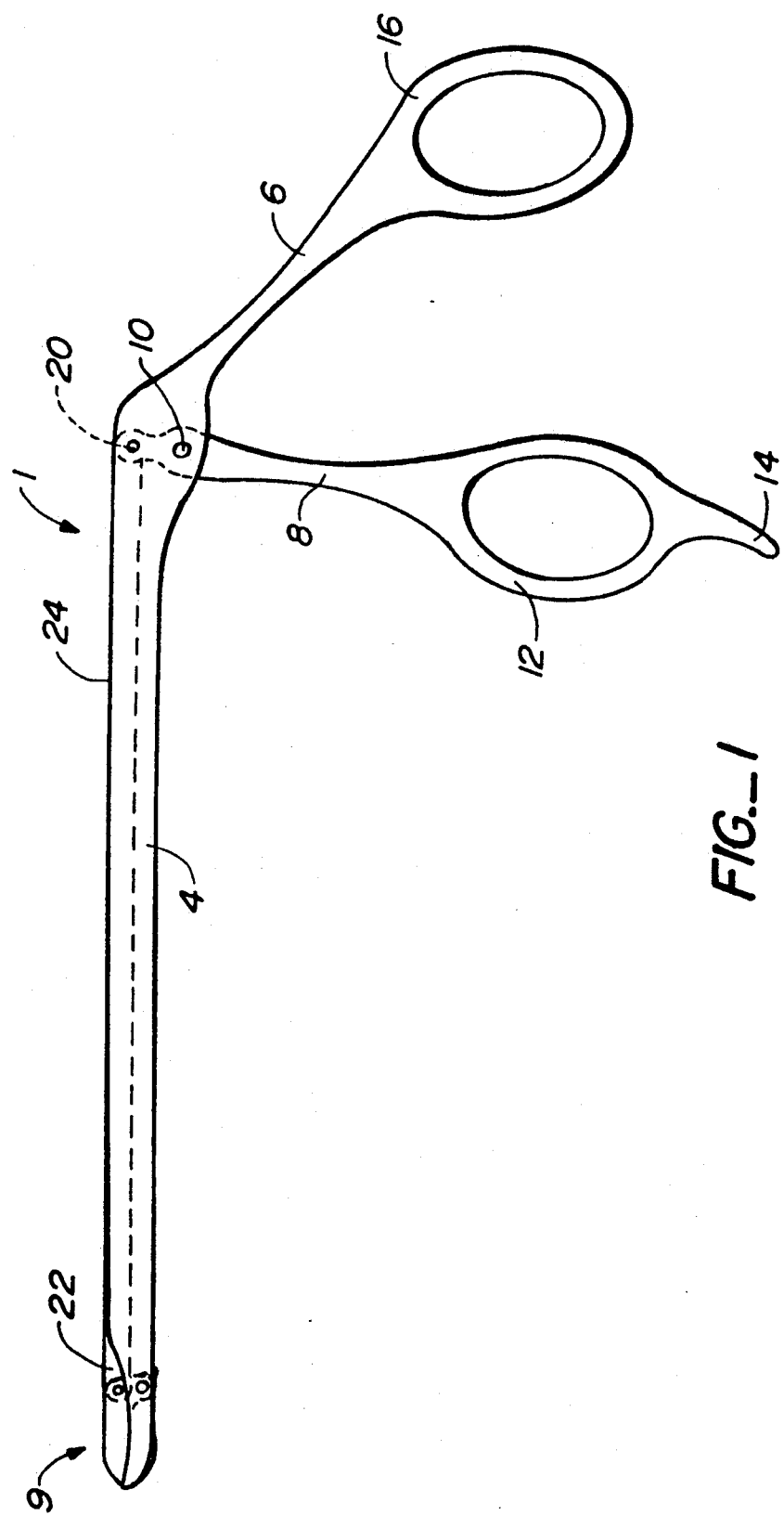
FIG._1

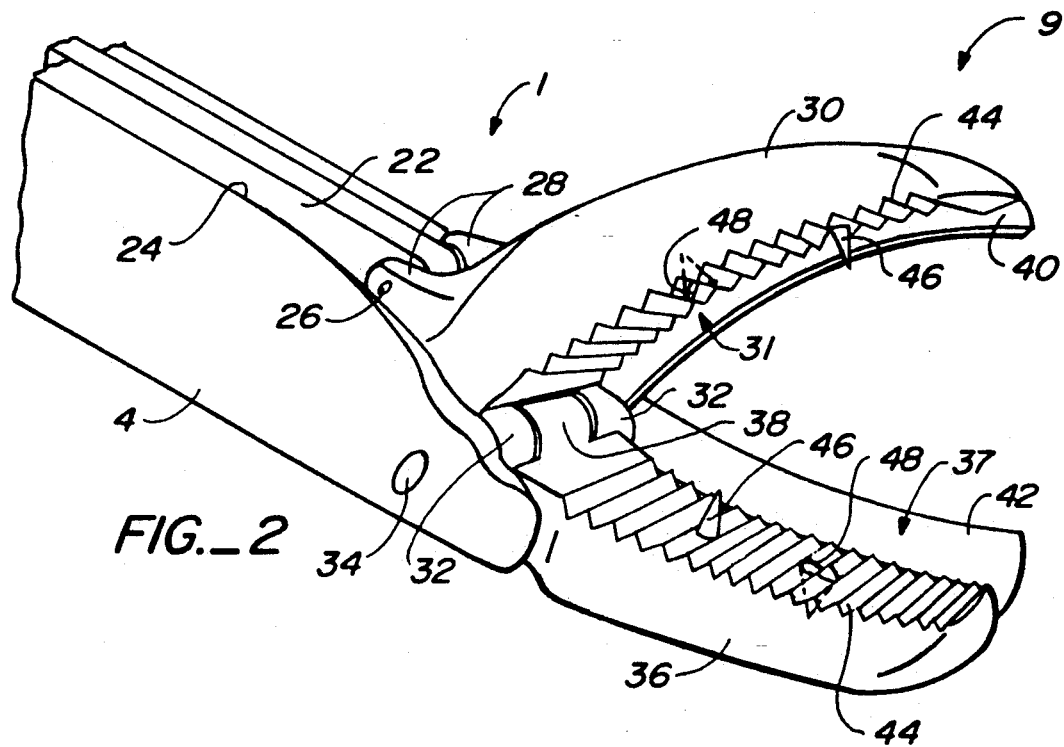
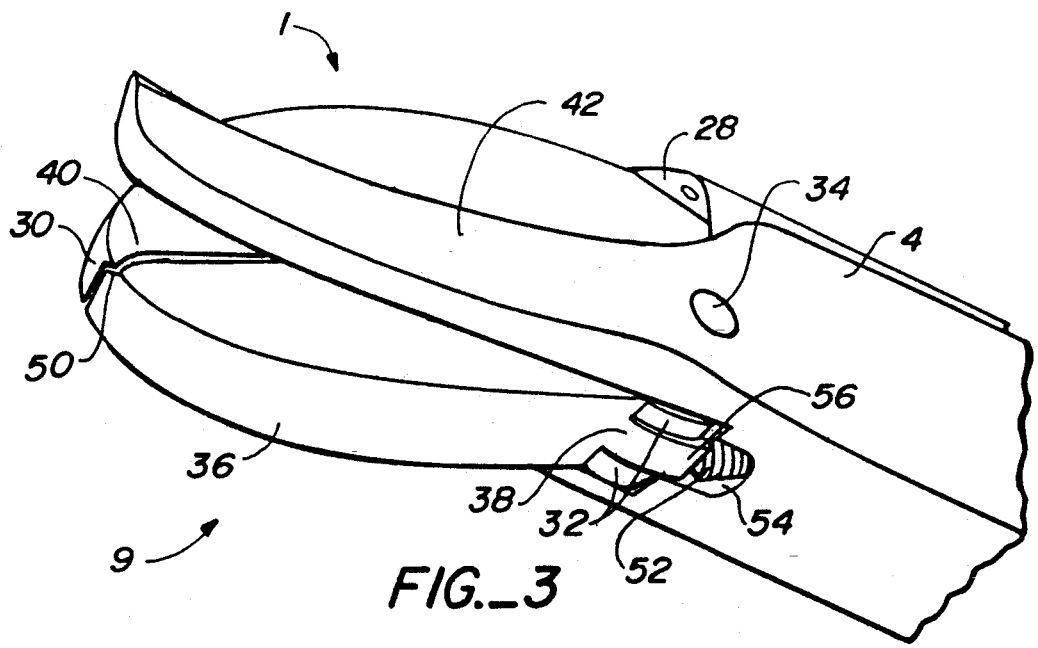

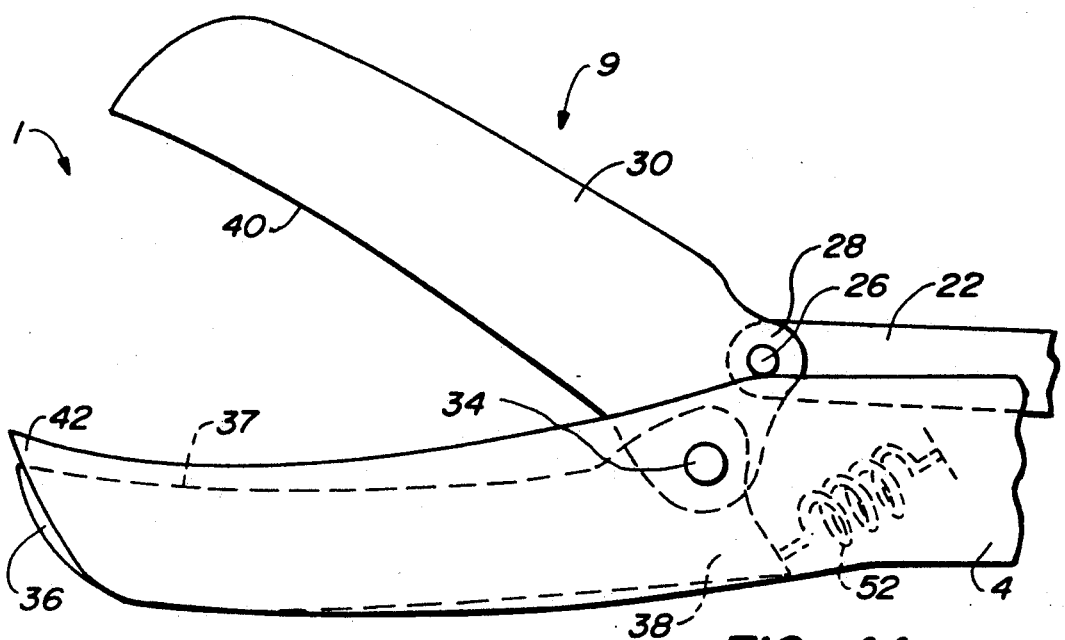
FIG._4A
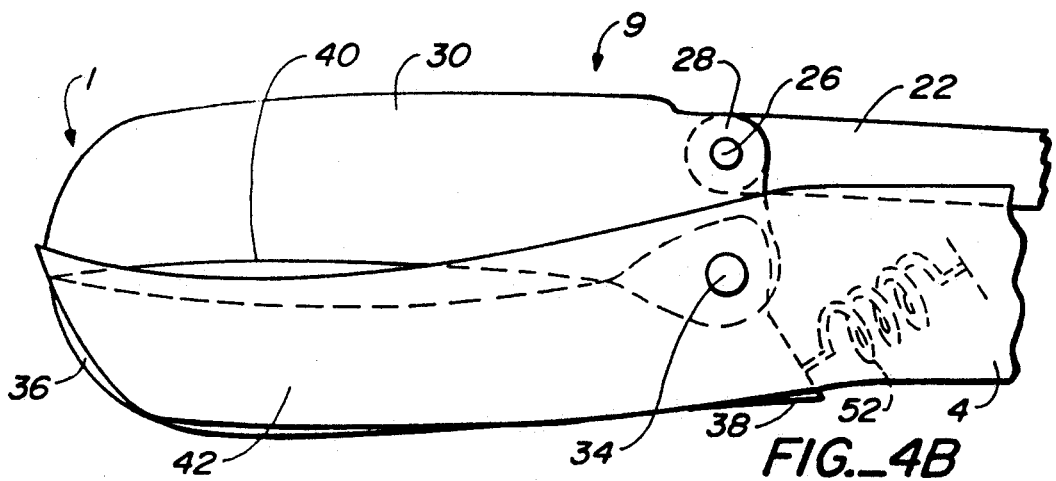
FIG._4B
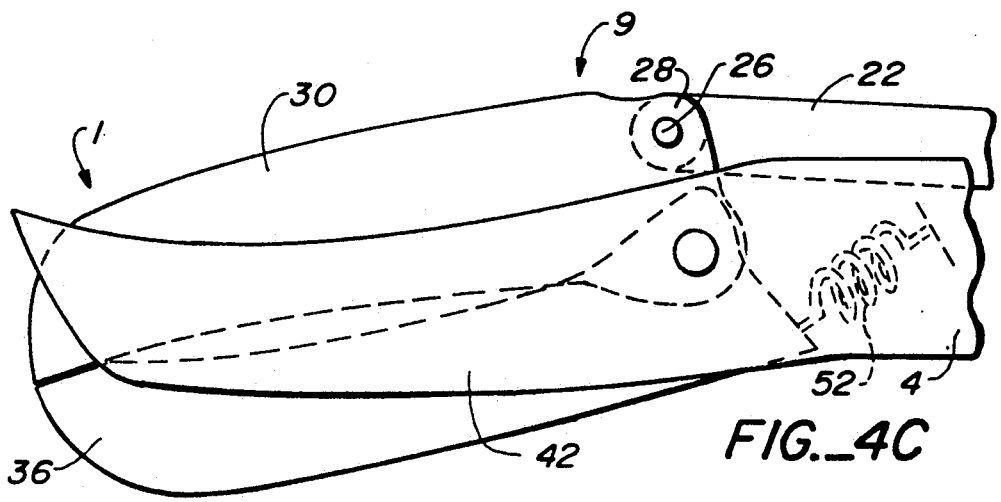
FIG._4C

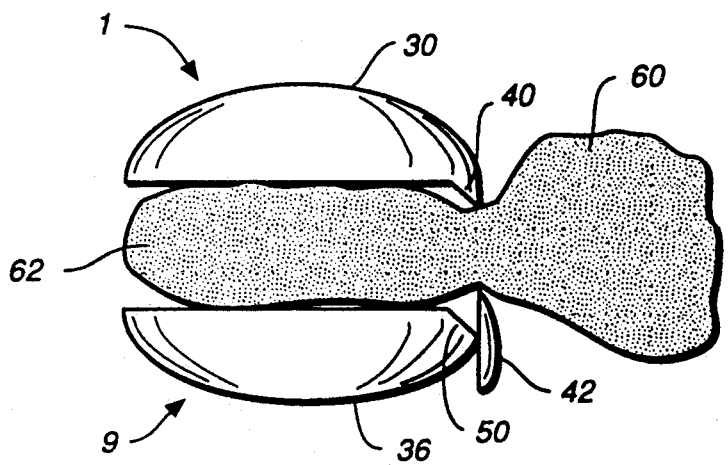
FIG._5A
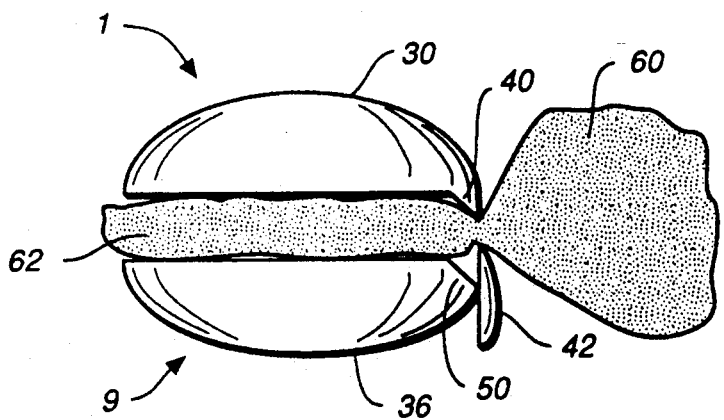
FIG._5B
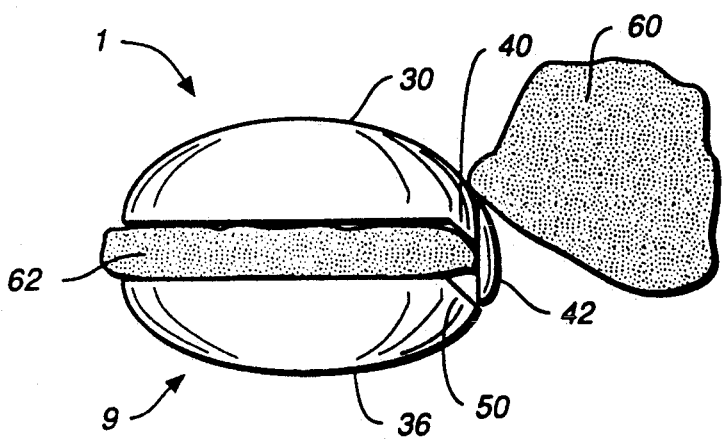
FIG._5C

ARTHROSCOPIC RESECTOR

FIELD OF THE INVENTION

This invention relates to surgical instruments, more particularly to an instrument which simultaneously clamps and transects tissue, usually for the removal thereof from a patient.

BACKGROUND OF THE INVENTION

Many surgical operations, for example, arthroscopic procedures and the like, require the surgeon to resect (i.e. cut and remove) small pieces of tissue from the body of the patient. Even though these pieces may be very tiny, it may be important that they not be dropped or otherwise mislaid so as to remain within the body cavity after the operation. For example, even small pieces of tissue can cause significant discomfort and pain if left within the interstices of human joints, where they may interfere with the healing and proper functioning of the joint—perhaps even causing further deterioration thereof. Alternatively, the procedure may involve a biopsy, wherein retaining the small piece may be critical for further diagnosis and treatment.

Furthermore, it is often important to accomplish surgical procedures in as quick, efficient and reliable a manner as is possible. Delay or error can result in complicating or serious consequences. While clamping the tissue with a pair of forceps (surgical pliers) and thereafter amputating it with a scalpel or the like may be crudely effective, this involves two separate instruments and a cumbersome and time-consuming series of operations. In some cases, there may not be enough room for both instruments—for example, within the interior of a human or animal joint.

Surgical instruments which save time and which free the hands of the surgeon for other functions can be of great aid in achieving successful surgery. Accordingly, the present invention provides an instrument which a surgeon may use to achieve both the clamping and the transection of tissue in a single stroke, using only one hand. Thereafter, the tissue may be securely removed from the body merely by withdrawing the instrument—no other manipulation of the tissue or the instrument is required.

Prior developments in this field may be generally illustrated by reference to the following patents:

| Patent No. | Patentee | Issue Date |
| --- | --- | --- |
| 4,600,007 | J. Lahodny | Jul. 15, 1986 |
| 4,452,246 | R. Bader et al. | Jun. 05, 1984 |
| 5,009,657 | J. Cotey et al. | Apr. 23, 1991 |
| 3,175,556 | E. Wood et al. | Mar. 30, 1965 |
| 2,025,345 | H. Harris | Dec. 24, 1935 |
| 4,674,501 | I. Greenberg | Jun. 23, 1987 |
| 4,770,174 | T. Luckman et al. | Sep. 13, 1988 |
| 4,944,093 | E. Falk | Jul. 31, 1990 |

U.S. Pat. Nos. 4,600,007, 3,175,556 and 4,452,246 teach scissor-like cutting instruments that have combination clamps and blades. However, the clamps and blades must be individually operated by separate controls in the handle area.

U.S. Pat. No. 5,009,657 teaches a instrument that has needle or tooth-like grips in one jaw and depressions in the other for receiving the grips.

The rest of the patents are representative of what is in the art.

SUMMARY OF THE INVENTION

The invention is a hand-held instrument for use in surgery which simultaneously transects and clamps onto a piece of tissue, in order that the piece may be secured and removed from the patient's body without premature loss thereof.

As used herein, "scissor-cutting" and similar phrases will refer to the action wherein a pair of blades, which are pivotally-coupled and pressed together, cut by rotating past each other in the manner of the blades of a pair of scissors. "Plier-clamping" and the like will refer to the action wherein a pair of jaws, which are pivotally-coupled together, clamp by rotating their faces toward each other into mutually-opposed contact with, or into close proximity to, one another in the manner of the jaws of a pair of pliers.

The instrument of this invention has set of opposed jaws that pivot about a common axis with respect to a shaft of the instrument's handle. The upper jaw has an upper blade or cutting surface rigidly affixed to or incorporated within one side thereof. A second (lower) blade is rigidly affixed to or incorporated within the handle shaft. When the upper jaw and upper blade are jointly forced to pivot downward, by a push rod journaled within the shaft, the rotating upper blade moves past the fixed lower blade to cut off a piece of tissue in scissor-cutting fashion. Of course, which blade is "fixed" and which blade "rotates" depends on the point of view of the observer. It will usually be convenient herein to refer to the lower blade as being "fixed," in that it does not move with respect to the shaft.

The lower jaw is simultaneously forced (by the thickness of the tissue) to rotate about its pivot downwardly, i.e. in the same direction as the upper jaw. This allows the jaws to clamp the tissue without allowing the relatively thick tissue to interfere with the cutting operation of the blades.

The lower jaw is held tightly against the interposed tissue by way of a spring. Stops built into the lower jaw and the handle shaft keep the spring under constant compression, even when the jaws of the instrument are in a fully open position. The spring causes the jaws to tightly clasp the tissue during and after its amputation from its point of attachment. In this manner, the piece of tissue is never loose. It may be removed from the body cavity without risk of its becoming lost therein. Furthermore, by proper selection of the tensile strength of the spring, excessive compression of the tissue sample may be prevented, should the sample need to be preserved.

The instrument is operated by a scissor handle arrangement. One finger grip portion thereof operates the push rod and the other finger grip portion steadies the shaft. The device may be reliably operated using a single hand.

Preferably, a complimentary pair of instruments will be available to the surgeon, one with blades on the right side thereof and one with blades on the left, so that the blade and jaw assembly may be orientated properly with respect to the desired point of amputation of the tissue.

FEATURES AND ADVANTAGES

An object of this invention is to disclose resector apparatus which includes a first jaw fixed in position with respect to a first blade. The apparatus includes a second jaw rotatable with respect to a second blade, the first and second blades rotatable together and apart with respect to each other in scissor-cutting fashion, the first and second jaws rotatable together and apart with respect to each other in plier-clamping fashion. The resector also includes spring means for allowing the second jaw and second blade to rotate in fixed tandem together with respect to the first jaw and first blade and also for allowing the second jaw and second blade to rotate apart with respect to each other automatically upon the second jaw receiving pressure tending toward such rotation apart with, respect to each other.

Other features of the disclosed resector are tissue-clamping means on the first and second jaws and rotating means for rotating the first and second blades together and apart with respect to each other in scissor-cutting fashion and for rotating the first and second jaws together and apart with respect to each other in plier-clamping fashion.

Yet another feature is the rotating means includes an opposed pair of legs rotatable inwardly and outwardly with respect to each other in scissor-leg fashion. The legs are operably connected to the first and second blades and to the first and second jaws.

Still another feature is the rotating means further includes a shaft having a longitudinal axis. The rotating means includes a push rod adjacent to the shaft and moveable longitudinally with respect to the axis of the shaft. The first blade is connected to a first pivot at a first end of the push rod. The second blade is fixedly connected to a first end of the shaft in pivotally-coupled scissor-cutting relationship with the first blade. The first jaw is connected to the first pivot and the second jaw is connected to the first end of the shaft in pivotally-coupled plier-clamping relationship with the first jaw and in pivotally rotatable relationship with respect to the second blade.

Another feature is the apparatus further includes a second pivot at the first end of the shaft, to which second pivot both the first jaw and the second jaw are rotatably attached.

A feature is the resector further includes a third pivot on a second end of the shaft, to which third pivot one leg is rotatably attached, the other leg being formed as an integral part of the second end of the shaft.

Still another feature is the apparatus includes a fourth pivot on the second end of the shaft, to which fourth pivot a second end of the push rod is attached.

Yet another feature is the spring means includes a spring captured in a well in the first end of the shaft, against which spring the second jaw is biased.

Another feature is an apparatus which is easy to use, attractive in appearance and suitable for mass production at relatively low cost.

Other novel features which are characteristic of the invention, as to organization and method of operation, together with further objects and advantages thereof will be better understood from the following description considered in connection with the accompanying drawing in which a preferred embodiment of the invention is illustrated by way of example. It is to be expressly understood, however, that the drawing is for the purpose of illustration and description only and is not intended as a definition of the limits of the invention.

Certain terminology and derivations thereof may be used in the following description for convenience in reference only and will not be limiting. For example, the words "upwardly," "downwardly," "leftwardly," and "rightwardly" will refer to directions in the drawings to which reference is made unless otherwise stated. Similarly, the words "inwardly" and "outwardly" will refer to directions toward and away from, respectively, the geometric center of a device and designated parts thereof.

BRIEF DESCRIPTION OF THE DRAWING

FIG. 1 is a frontal elevation of a resector of this invention;

FIG. 2 is a fragmentary perspective view of the distal end of the resector of FIG. 1, taken from above with the jaw and blade assembly thereof in an open position;

FIG. 3 is a fragmentary perspective view of the same resector, taken from below with the jaw and blade assembly in a closed position;

FIGS. 4A–4C are schematic fragmentary frontal elevations of the resector, illustrating the closing of the jaws and the blades in linear time sequence; and FIGS. 5A–5C are schematic fragmentary end elevations of the resector, illustrating the amputation of tissue in linear time sequence.

Drawing Reference Numerals

1: resector
4: shaft
6: leg
8: leg
9: jaw and blade assembly
10: pivot for 6, 8
12: loop on 8
14: flange on 12
16: loop on 6
20: pivot for 8, 22
22: push rod
24: channel in 4 for 22
26: pivot for 22, 30
28: upper lugs of 30
30: upper jaw
31: lower face of 30
32: lower lugs of 30
34: pivot for 4, 30, 36
36: lower jaw
37: upper face of 36
38: lug of 36
40: upper blade on 30
42: lower blade on 4
44: serrations on 30, 36
46: barbs on 30, 36
48: wells for 46
50: bevel on 36
52: spring
54: well in 4 for 52
56: stop on 38 for 52
60: tissue
62: tissue

DESCRIPTION OF A PREFERRED EMBODIMENT

Referring to FIG. 1, there is illustrated therein a resector 1 of this invention. It is anticipated that resector 1 will be of particular benefit when performing arthroscopic procedures.

The resector 1 is generally comprised of a shaft 4; a pair of scissor-like legs 6 and 8 on the proximal end of the shaft (the legs and shaft generally comprising a handle portion); and a jaw and blade assembly 9 on the distal end of the shaft. The legs are operably connected to the jaw and blade assembly by means of the shaft and a push rod 22. The legs act as levers whose movement is translated to the jaw and blade assembly by means of the push rod, as described below.

In many applications, the instrument will be constructed with relatively minute dimensions in order to provide access to tight places, i.e. the combined height of the jaws 30 and 36 may be only 8 mm, or even less.

The legs 6 and 8 rotate inwardly and outwardly with respect to each other about a first pivot 10 in scissor-leg fashion. The pivot 10 can be a screw, pin, rivet or the like. Finger loops 12 and 16 are formed in the ends of legs 8 and 6, respectively. Leg 8 may have a downwardly-depending supplemental finger flange 14. Although shown in the drawing as being connected to the shaft 4 at a skewed angle, the legs 6 and 8 could just as easily be configured so that the shaft bisects the angle of intersection of their axes.

The leg 6 is formed as an integral extension of the shaft 4 and does not move with respect thereto. The leg 8 rotates about the pivot 10 with respect to the shaft 4 and the leg 6. This movement, in turn, forces the push rod 22 back and forth, i.e. longitudinally with respect to the axis of the shaft, within a channel or groove 24 formed in the upper portion of the shaft 4. The upper portion of the leg 8 (i.e. the portion located above the pivot 10) acts as a lever with respect to the push rod 22. The upper portion of the leg 8 and the proximal end of the push rod 22 are rotatably connected together by means of a second pivot 20. The legs 6 and 8, together with the shaft 4 and push rod 22, comprise means for rotating together and apart, with respect to each other, the components of the blade and jaw assembly 9.

Turning to FIGS. 2 and 3, the operation of the jaw and blade assembly 9 will be described with reference thereto. A third pivot 26 rotatably interconnects the distal end of the push rod 22 with an opposed pair of upper lugs 28 formed on the proximal end of an upper jaw 30. Longitudinal translation back and forth of the push rod, accomplished by operating the legs 6 and 8 in a scissors-like fashion, causes the upper jaw 30 to rotate about a fourth pivot 34. The upper jaw 30 is rotatably connected to the pivot 34 by means of an opposed pair of lower lugs 32. Captured between the lower lugs 32 of the upper jaw 30, so as to rotate about the same pivot 34, is a lug 38 formed on the proximal end of a lower jaw 36.

One side of the upper jaw 30 is formed into a downwardly-depending upper blade or cutting surface 40. Alternatively, the upper blade 40 may be a separate piece of hardened steel which is welded, screwed or riveted to the side of the upper jaw 30. In any event, the blade 40 is fixed in position with respect to the upper jaw.

Interacting in scissors-like fashion with the upper blade 40 is a lower blade 42. As perhaps best seen in FIG. 3, the lower blade 42 is an integral extension of the shaft 4 and is immobile with respect thereto; although it, too, could be a hardened piece fixedly attached, in this case, to the shaft 4. Parallel sets of grooved serrations 44 traverse the opposed faces 31 and 37 of the jaws 30 and 36, respectively. The serrations 44 are adapted to firmly grip interposed tissue in the manner of serrations on pliers, forceps and similar tools. One or more barbs 46 on each jaw face 31 and 37 may interconnect with a barb-receiving well or wells 48 on the opposite jaw face. This further assures a firm grip on tissue, both before and after the amputation thereof as discussed below. The jaw faces 31 and 37, with or without the serrations 44 and barbs 46, comprise tissue-clamping means.

An inclined notch or bevel 50 may be introduced on the blade-facing side of the lower jaw 36 for the reception of a congruent portion of the upper blade 40. However, in most cases, the clamped tissue will be so thick as to prevent the reception of the upper blade 40 within the space formed by the bevel 50. Furthermore, the serrated faces of the jaws 30 and 36 are preferably each concave, so as best to receive thick tissue in the center thereof, in the manner of pliers or crab claws. Therefore, it is anticipated that the jaws 30 and 36 would only touch at the outermost and innermost ends thereof, if at all, when clamping tissue. However, for some procedures, it may be appropriate to provide a resector 1 having flat, rather than concave, serrated faces that flushly interconnect, and, in that case, the cooperation of the bevel 50 and the upper blade 40 could become more important. Alternatively, it might be appropriate to form the upper blade or cutting surface 40 so as not to depend downwardly from the upper jaw 30, in which case no bevel 50 would be needed on the lower jaw 36.

A compression-resistant spring 52 is captured in a well 54 formed in the distal end of the underside of the shaft 4. The spring 52 is biased against a stop 56 formed on the lug 38 of the lower jaw 36.

The operation of the jaw and blade assembly 9 can perhaps best be understood by referring to the series of successive views shown in FIGS. 4A-4C, which show the closing thereof in linear progression.

FIG. 4A shows the instrument 1 in a fully open position, which position is receptive to receiving tissue to be amputated. The upper jaw 30 is fully opened (i.e. it is rotated to its maximum extent clockwise with respect to the shaft 4) by retracting the push rod 22—through manipulation thereof by the thumb and forefinger or index finger of a single hand of the surgeon, which fingers have been inserted in loops 16 and 12, respectively.

In FIG. 4A, the lower jaw 36 is automatically pushed forward as far as it can go clockwise (with respect to the shaft 4) by the action of the spring 52 against its lug 38. Suitable stops (not illustrated) can be incorporated into the lower jaw 36 and the shaft 4 to limit the extent that the lower jaw can travel in a clockwise direction.

Still referring to FIG. 4A, the upper and lower blades 40 and 42 are separated to their maximum extent by the retraction of the push rod 22. In this position, the upper face 37 of the lower jaw 36 is retracted down only slightly from the cutting edge of the lower blade 42. This allows tissue at the point of amputation to be touched first by the blades 40 and 42 (for the accurate placement thereof), but next to be promptly grasped by the jaws 30 and 36 upon movement together of the scissor legs 6 and 8. Alternatively, the instrument could be configured, as noted above, so that the blades 40 and 42 would start flush with the jaw faces 31 and 37, if it were to be desired that the tissue be clamped before or simultaneously with the initiation of cutting action.

FIG. 4B shows the position of the jaw and blade assembly 9 after the push rod 22 has been extended out far enough to cause the innermost and outermost tips of the jaws 30 and 36 to touch, thereby limiting further rotation of the jaws toward each other. Some cutting action has been initiated at the periphery of the blades 40 and 42. However, were the lower jaw 36 stationary with respect to the lower blade 42, it can be seen that the cutting action would cease in the position of FIG. 4B and would be incomplete at the center of the blades 40 and 42.

However, as can be seen in FIG. 4C, further extension of the push rod 22 will force the upper jaw 30 and lower jaw 36 to travel together counterclockwise by causing the spring 52 to compress within its well 54. Thus, it can be seen that the spring 52 comprises means for keeping the lower jaw 36 and lower blade 42 stationary with respect to each other when the face 37 of the lower jaw is not under pressure (or, if the upper jaw 30 and upper blade 40 are viewed as "fixed", means for allowing the lower jaw 36 and lower blade 42 to rotate in fixed tandem together with respect thereto). Upon receiving pressure from trapped tissue, however, the lower jaw and lower blade automatically begin to rotate apart past each other. At the same time, the lower blade 42 continues to rotate with respect to the upper jaw 30 and upper blade 40.

At the maximum extent of counterclockwise travel of the jaw pair 30 and 36, the blades 42 and 40 will have completely passed each other. This accomplishes complete amputation of any tissue interposed in the jaws 30 and 36.

FIGS. 5A-5C are a similar sequence of views of successive positions of the instrument, this time in a series of end views showing the interposition of tissue 62 that is desired to be resected from tissue 60 (reference being made where necessary to parts best shown in the previous figures).

FIG. 5A shows the resector 1 in a partially open position, in which position it has just received and clamped tissue 62 which the surgeon desires to amputate from tissue 60.

In FIG. 5A, the lower jaw 36 is still pushed upward about as far as it can go by the action of the spring 52. The upper and lower blades 40 and 42 are still separated—although they have contacted tissues 60 and 62 at the point of desired amputation, and cutting has begun.

FIG. 5B shows the position of the jaw and blade assembly 9 after the push rod 22 has been extended far enough to compress the tissue 62 as much as possible without initiating significant compression of the spring 52. In point of fact, the spring 52 will begin to deform immediately upon receiving pressure from interposed tissue. However, the amount of deformation will be slight until the tissue 62 has been significantly compressed (unless, of course, a spring of very low tensile strength is used). Note that the particular piece of tissue 62 illustrated in FIG. 5 is too thick or dense to allow the tips of the jaws 30 and 36 ever to touch. Without the unique spring-activated rotating action of the lower jaw 36 disclosed herein, amputation of the piece of tissue 62 from tissue 60 would be unsuccessful.

However, as can be seen in FIG. 5C, further extension of the push rod 22 forces the upper jaw 30 and lower jaw 36 to travel downward together, pretty much in fixed tandem, by causing the spring 52 to compress within its well 54. At the maximum extent of travel of the jaw pair 30 and 36 illustrated, the cutting surfaces of the blades 42 and 40 have completely passed each other. This has accomplished the complete amputation of all tissue 62 interposed within the jaws 30 and 36. At this point, the amputated tissue 62 is both severed and securely clamped for the safe removal thereof from the patient's body.

Of course, the legs 6 and 8 could automatically be held closed by the type of interlocking serrated clasp mechanism which is so well known in the art of forceps as not to require separate illustration. See, for example, the locking indentations 8 of U.S. Pat. No. 4,600,007, above.

It can be seen that the entire operation has been accomplished in one scissor stroke, using only one of the surgeon's hands. Both the cutting and the clamping functions automatically are carried out simultaneously. The entire procedure is simplicity itself, requiring minimal training.

While the above provides a full and complete disclosure of the preferred embodiments of this invention, various modifications, alternate constructions, and equivalents may be employed without departing from the true spirit and scope of the invention. Such changes might involve alternate materials, components, structural arrangements, sizes, operational features or the like.

For example, the upper jaw might also be fitted with a compression spring so as to be retractable upward with respect to the upper blade—in the manner of the relationship between the lower blade and lower jaw. Furthermore, by eliminating the elongated shaft and the push rod, the instrument might be fashioned in the manner of traditional scissors or forceps, i.e. perhaps with only one pivot. The invention thus might be said to most broadly reside in the combination of one jaw and blade pair being fixed together, which pair pivots toward a second jaw and blade pair—the second jaw and blade pair normally travelling together but being able to rotate with respect to each other when the jaws are under pressure. Therefore, the above description and illustrations should not be construed as limiting the scope of the invention which is defined by the appended claims.

What is claimed is:

1. Resector apparatus including:

a first blade;

a first jaw fixed in position with respect to the first blade;

a second blade;

a second jaw rotatable with respect to the second blade, the first and second blades rotatable together and apart with respect to each other in scissor-cutting relationship, the first and second jaws rotatable together and apart with respect to each other in plier-clamping relationship;

tissue-clamping means on the first and second jaws;

spring means for allowing the second jaw and second blade to rotate in fixed tandem together with respect to the first jaw and first blade and also for allowing the second jaw and second blade to rotate apart with respect to each other automatically upon the second jaw receiving pressure tending toward such rotation apart with respect to each other;

rotating means for rotating the first and second blades together and apart with respect to each other in said scissor-cutting relationship and for rotating the first and secodn jaws together and apart with respect to each other in said plier-clamping relationship;

an elongated shaft separating the rotating means from the jaws and blades, the shaft operatively interconnecting the rotating means with the jaws and the blades, the shaft having a longitudinal axis and a first shaft end;

an opposed pair of legs included in the rotating means, the legs rotatable inwardly and outwardly with respect to each other in scissor-leg relationship, the legs operably connected by the shaft to the first and second blades and to the first and second jaws;

the rotating means having a first pivot; and a push rod included in the rotating means adjacent to the shaft and moveable longitudinally with respect to the axis of the shaft, the push rod having a first push rod end, the first blade connected to the first pivot at the first push rod end, the second blade fixedly connected to the first shaft end in pivotally-coupled scissor-cutting relationship with the first blade, the first jaw connected to the first pivot, and the second jaw connected to the first shaft end in pivotally-coupled plier-clamping relationship with the first jaw and in pivotally-rotatable relationship with respect to the second blade.

2. The apparatus of claim 1 further including:
a second pivot at the first shaft end, to which second pivot both the first jaw and the second jaw are rotatably attached.

3. The apparatus of claim 2 further including:
a second shaft end on the shaft; and
a third pivot on the second shaft end, to which third pivot one leg is rotatably attached, the other leg being formed as an integral part of the second shaft end.

4. The apparatus of claim 3 further including:
a second push rod end on the push rod; and
a fourth pivot on said second push rod end, to which fourth pivot said one leg is attached.

5. The apparatus of claim 3 further including:
a well formed in the first shaft end, and wherein the spring means includes
a spring captured in the well, against which spring the second jaw is biased.

6. Resector apparatus including:
a shaft having a longitudinal axis and a distal shaft end;
a push rod having a distal push rod end, the push rod journaled within the shaft and translatable longitudinally with respect to the axis of the shaft;
a first pivot at the distal push rod end;
an upper blade connected to the first pivot;
a lower blade fixedly connected tot he distal shaft end in pivotally-coupled cutting relationship with the upper blade;
an upper jaw connected to the first pivot; and
a lower jaw connected to the distal shaft end in pivotally-coupled clamping relationship with the upper jaw and in pivotally-rotatable relationship with respect to the lower blade.

7. The apparatus of claim 6 further including:
a second pivot at the distal shaft end, to which second pivot both the upper jaw and the lower jaw are rotatably attached.

8. The apparatus of claim 7 further including:
a proximal shaft end on the shaft;
serrated faces on the jaws;
an opposed pair of legs rotatable inwardly and outwardly with respect to each other in scissor-leg relationship; and
a third pivot on the proximal shaft end, to which third pivot one leg is rotatably attached, the other leg being formed as an integral part of the proximal shaft end.

9. The apparatus of claim 8 further including:
a proximal push rod end on the push rod; and
a fourth pivot on said proximal push rod end, to which fourth pivot said one leg is attached.

10. The apparatus of claim 8 further including:
a well formed in the distal shaft end; and
a spring captured in the well, against which spring the lower jaw is biased.

11. Resector apparatus including:
a shaft having a longitudinal axis and distal and proximal shaft ends, the shaft forming a channel within itself;
a push rod having distal and proximal push rod ends, the push rod captured within the channel in the shaft and moveable longitudinally with respect to the axis of the shaft;
a first pivot at the distal push rod end;
a first blade connected to the first pivot;
a second blade fixedly connected to the distal shaft end in pivotal scissor-cutting relationship with the first blade;
a first jaw connected to the first pivot;
a second jaw connected to the distal shaft end in pivotal plier-clamping relationship with the first jaw and in pivotally-rotatable relationship with respect to the second blade;
a second pivot at the distal shaft end, to which second pivot both the first jaw and the second jaw are rotatably attached;
an opposed pair of first and second legs rotatable with respect to each other in scissor-leg relationship;
a third pivot on the proximal shaft end, to which third pivot the first leg is rotatably attached, the second leg being formed as an integral extension of the proximal shaft end; and
a fourth pivot on said proximal push rod end, to which fourth pivot said first leg is attached.

12. The apparatus of claim 11 further including:
a well formed in the distal shaft end; and
a spring captured in the well, against which spring the second jaw is biased.

* * * * *